United States Patent
Solladie et al.

(10) Patent No.: US 6,278,001 B1
(45) Date of Patent: Aug. 21, 2001

(54) METHOD FOR PREPARING (+) COMPACTIN AND (+) MEVINOLIN ANALOG COMPOUNDS HAVING A β-HYDROXY-δ-LACTONE GROUPING

(75) Inventors: Guy Solladie; Claude Bauder, both of Strasbourg (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 08/875,446

(22) PCT Filed: Nov. 12, 1996

(86) PCT No.: PCT/FR96/01782

§ 371 Date: Oct. 8, 1997

§ 102(e) Date: Oct. 8, 1997

(87) PCT Pub. No.: WO97/19917

PCT Pub. Date: Jun. 5, 1997

(30) Foreign Application Priority Data

Nov. 28, 1995 (FR) .................................................. 95 14083

(51) Int. Cl.⁷ ................................................. C07D 309/30
(52) U.S. Cl. ............................................................. 549/292
(58) Field of Search ................................ 560/11; 549/292

(56) References Cited

PUBLICATIONS

G. Solladie et al., Tetrahedron: Asymmetry, 6(11):2679–2682 (1995).
G. Solladie et al., Journal of Organic Chemistry, 60(24):7774–7777 (1995).
G. Solladie et al., Tetrahedron Letters, 33(12):1605–1608 (1992).
G. Solladie et al., Tetrahedron: Asymmetry, 3(1):33–38 (1992).
G. Solladie et al., Tetrahedron: Asymmetry, 5(9):1717–1726 (1994).
G. Wess et al., Tetrahedron Letters, 31(18):2545–2548 (1990).
K. Prasad et al., Tetrahedron: Asymmetry, 1(5):307–310 (1990).
K. Prasad et al., Tetrahedron Letters, 25(23):2435–2438 (1984).

*Primary Examiner*—Samuel Barts
(74) *Attorney, Agent, or Firm*—Finnegan, Henderson, Farabow, Garrett & Dunner, L.L.P.

(57) ABSTRACT

A novel method for preparing (+)compactin and (+)mevinolin analog compounds having a β-hydroxy-δ-lactone grouping is disclosed. The method for preparing said compounds uses novel reaction intermediates. Said reaction intermediates and the respective methods for preparing same are also disclosed.

1 Claim, No Drawings

METHOD FOR PREPARING (+) COMPACTIN AND (+) MEVINOLIN ANALOG COMPOUNDS HAVING A β-HYDROXY-δ-LACTONE GROUPING

The invention relates to a new process for preparing compounds containing a β-hydroxy-δ-lactone group which are (+)-compactin and (+)-mevinolin analogues. The process for preparing these products involves new reaction intermediates which are also subjects of the invention, as are the respective processes for preparing them.

HMG-coenzyme A reductase (β-hydroxy-β-methylglutaryl-coenzyme A reductase, hereinafter designated HMG-CoA reductase) inhibitors, to which family (+)-compactin and (+)-mevinolin belong, are pharmaceutical active agents used orally in the treatment of hypercholesterolaemia (excessively high plasma cholesterol levels). See, in this connection, the document "Pharmacologie, Des concepts fondamentaux aux applications thérapeutiques" [Pharmacology, From fundamental concepts to therapeutic applications], published under the direction of M. Schorderet, Editions Frison-Roche, second edition, 1992.

These inhibitors are also used in the treatment of diseases associated with the excessive presence of cholesterol, such as arteriosclerosis.

(+)-Compactin (formula 1 below with R=H) and (+)-mevinolin (formula 1 with R=CH$_3$) are molecules which are well known for their HMG-CoA reductase inhibiting activity:

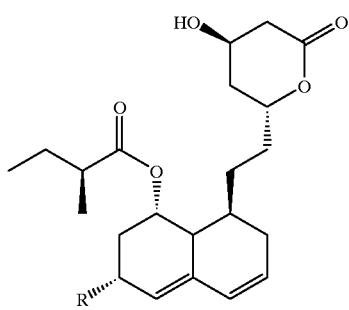

(1)

In addition, a large amount of work has been developed around the lactone fragment of these molecules. In particular, a review of the syntheses of (+)-compactin and (+)-mevinolin analogues is to be found in the documents Chapleur, Y. "Progress in the chemical synthesis of antibiotics and related microbial products", Springer Verlag 1993, vol. 2, 829–937 (Doc I) and T. Rosen and C. H. Heathcock, Tetrahedron, Vol. 42, No. 18, 4909–4951, 1986 (Doc II), which analogues have retained the lactone fragment of (+)-compactin and of (+)-mevinolin and possess a lipophilic portion which is simplified relative to the latter compounds. However, none of the synthesis routes known for such molecules is satisfactory.

The main synthesis routes for the lactone fragment of the lactone 1, in optically active form, use chiral commercial starting materials such as maleic acid or 2-glutamic acid (M. Majewski et al., Tet. Lett. 1984, 25, 2101; T. Minami et al., Tet. Lett. 1993, 34, 513) or carbohydrates (M. Menges et al., Synlett 1993, 901;M. S. Ernolenko et al., Tet. Lett. 1994, 35, 715). Others comprise an asymmetric reduction step with rhodium-based catalysts (M. Terada et al., Tet. Lett. 1991, 32, 935; L. Shao et al., Tet. Lett. 1991, 32, 7699) or enzymatic reducing agents (F. Bennet et al., J. Chem. Soc. Perkin Transfer I, 1991, 133; M. H. Ansari, Tet. Lett. 1993, 34, 8271).

These syntheses are not without their drawbacks. In particular, the chiral starting materials employed in some of these syntheses are expensive, and catalysts enabling an asymmetric reduction to be induced are likewise very expensive. Moreover, enzymatic asymmetric reductions give enantiomeric excesses which do not exceed 80%.

Syntheses which do not have these drawbacks are also known, such as the one described in Tet. Lett., Vol. 35, No. 5, 715–718, 1994, but necessitate the use of dangerous reactants and solvents such as pyridine and tributyltin.

Thus, the applicant was surprised to discover a new synthesis route for (+)-compactin and (+)-mevinolin analogues. This synthesis route, which is easy to carry out and can be extrapolated to the industrial scale, uses an inexpensive starting material, a chiral agent which can be manufactured industrially and is of moderate cost. Furthermore, the method affords good yields, and the products of this synthesis are obtained with an excellent enantiomeric purity (>98%). In addition, this synthesis route enables access to be gained to new (+)-compactin and (+)-mevinolin analogues.

The subject of the invention is a new process for preparing the products corresponding to one of the formulae (Ia) and (Ib):

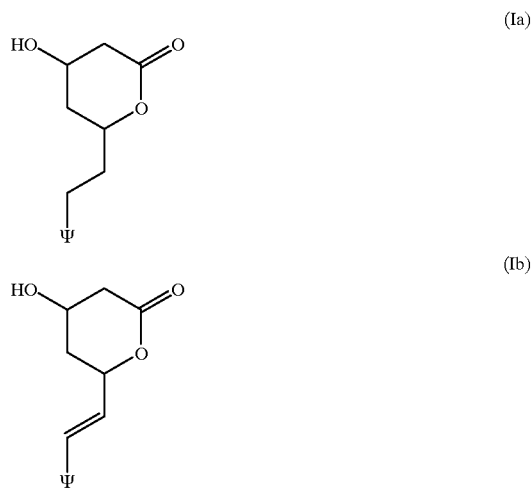

in which Ψ represents a radical chosen from:
saturated or unsaturated, linear, branched or cyclic C$_1$–C$_{40}$ alkyls, optionally interrupted by ether bridges and/or optionally substituted with one or more substituents chosen from halogen, hydroxyl, C$_1$–C$_{20}$ alkoxy, C$_1$–C$_{20}$ acyloxy, primary, secondary or tertiary amino, nitro, thiol, carboxyl, amido, C$_1$–C$_{20}$ alkyl carboxylate, aryl carboxylate, C$_1$–C$_{20}$ aralkyl carboxylate, C$_1$–C$_{20}$ alkylamido, arylamido and C$_1$–C$_{20}$ aralkylamido groups, and from aryl radicals and saturated or unsaturated C$_1$–C$_{20}$ nitrogen, oxygen, phosphorus and sulphur heterocycles;

aryls, optionally substituted with one or more substituents chosen from halogen, hydroxyl, C$_1$–C$_{20}$ alkoxy, C$_1$–C$_{20}$ acyloxy, amino, C$_1$–C$_{20}$ alkylamino and dialkylamino, nitro, thiol, carboxyl, amido, C$_1$–C$_{20}$ alkyl carboxylate, aryl carboxylate, C$_1$–C$_{20}$ aralkyl carboxylate, C$_1$–C$_{20}$ alkylamido, arylamido, C$_1$–C$_{20}$ aralkylamido and C$_1$–C$_{20}$ aryl groups, and from saturated or unsaturated, linear, branched or cyclic C$_1$–C$_{20}$ alkyl and aralkyl radicals and saturated or unsaturated C$_1$–C$_{20}$ nitrogen, oxygen, phosphorus and sulphur heterocycles;

aralkyls, optionally substituted with one or more substituents chosen from halogen, hydroxyl, $C_1$–$C_{20}$ alkoxy, $C_1$–$C_{20}$ acyloxy, amino, $C_1$–$C_{20}$ alkylamino and dialkylamino, nitro, thiol, carboxylic acid, amido, $C_1$–$C_{20}$ alkyl carboxylate, aryl carboxylate, $C_1$–$C_{20}$ aralkyl carboxylate, $C_1$–$C_{20}$ alkylamido, arylamido, $C_1$–$C_{20}$ aralkylamido and $C_1$–$C_{20}$ aryl groups, and from saturated or unsaturated, linear, branched or cyclic $C_1$–$C_{20}$ alkyl and aralkyl radicals;

nitrogen, oxygen, phosphorus or sulphur heterocycles, optionally substituted with one or more substituents chosen from halogen, hydroxyl, $C_1$–$C_{20}$ alkoxy, $C_1$–$C_{20}$ acyloxy, primary, secondary or tertiary amino, nitro, thiol, carboxylic acid, amido, $C_1$–$C_{20}$ alkyl carboxylate, aryl carboxylate, $C_1$–$C_{20}$ aralkyl carboxylate, $C_1$–$C_{20}$ alkylamido, arylamido and $C_1$–$C_{20}$ aralkylamido groups, and from aryl and aralkyl radicals and saturated or unsaturated $C_1$–$C_{20}$ nitrogen, oxygen and sulphur heterocycles.

The formulae (Ia) and (Ib) cover a very large number of products, the extent of which in the field of HMG-coenzyme A reductase inhibitors is illustrated by the documents "Progress in the chemical synthesis of Antibiotics and related microbial products", Y. Chapleur, Vol. 2, 1993, 829–937, G. Lukacs Ed. Springer Verlag (Doc I); T. Rosen and C. H. Heathcock, Tetrahedron, Vol. 42, No. 18, 4909–4951, 1986 (Doc II) and J. Prous "The year's drug news, therapeutic targets, 1994 edition", Prous science Publishers (Doc III). Besides the products mentioned in these documents, the process which is the subject of the present invention permits ready access to many other molecules corresponding to the formulae Ia and Ib.

Among the radicals represented by Ψ, there may be mentioned, for example, the radicals corresponding to the following formulae and which correspond to the products of formula (Ia) which are known to be HMG-coenzyme A reductase inhibitors:

Described in Doc I:

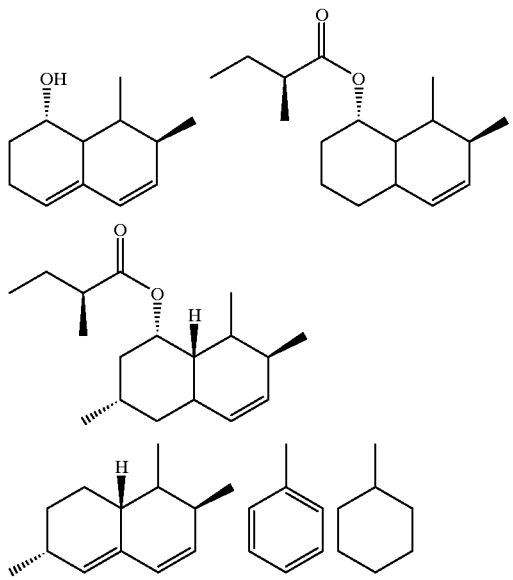

Described in Doc III:

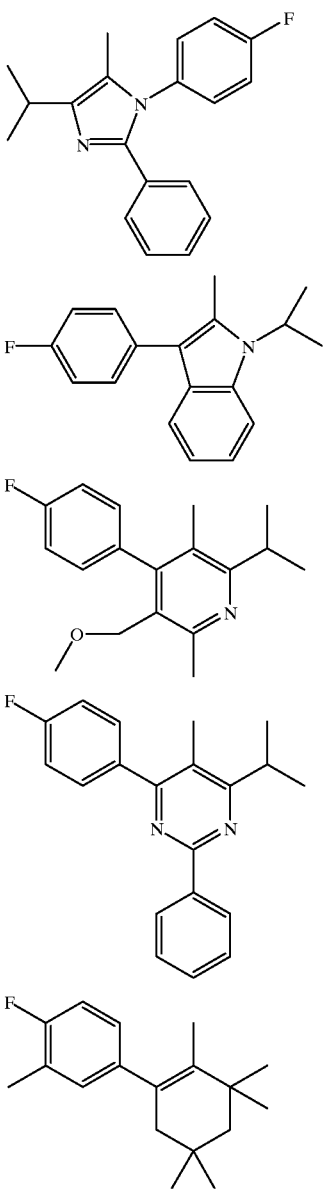

The products of formula (Ia) and of formula (Ib) contain at least two asymmetric carbons. Thus, the subject of the invention is a process for preparing each of the four diastereoisomers corresponding to one of the formulae (Ia) or (Ib), taken separately, as well as the mixtures thereof, racemic or otherwise.

The subject of the invention is a process for preparing the products of formula (Ia) and (Ib) characterized in that:

1) in a first step, the tri-anion of the alkyl 3,5-dioxohexanoate of formula (X) shown below is reacted with (−)- or (+)-menthyl (X's)-p-toluenesulphinate (p-toluene designated pTol) to obtain the alkyl (Xs)-3,5-dioxo-6-(p-tolylsulphinyl)hexanoate of formula (II), $$Y\text{—CO—}CH_2\text{—CO—}CH_2\text{—CO—}CH_3 \qquad (X)$$

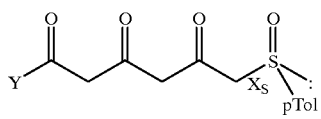

(II)

Xs and X's denoting the R or S configurations of the sulphur in the two molecules, with Xs≠X's, Y representing a saturated or unsaturated, linear or branched $C_1$–$C_{18}$ alkyloxy radical, an aryloxy radical or a $C_1$–$C_{18}$ aralkyloxy radical, an imidazolide radical, a saturated or unsaturated, linear or branched $C_1$–$C_{18}$ alkyl sulphide radical, an aryl sulphide or $C_1$–$C_{18}$ aralkyl sulphide radical or a radical

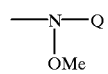

Q denoting a saturated or unsaturated, linear or branched $C_1$–$C_{18}$ alkyl radical.

Irrespective of the choice of Y, the group —COY will be assigned the name of ester, 2) in a second step, the 5-carbonyl function of the alkyl (Xs)-3,5-dioxo-6-(para-tolylsulphinyl)hexanoate is reduced enantioselectively to alcohol to give the alkyl [5($X_5$),S(Xs)]-5-hydroxy-3-oxo-6-(para-tolylsulphinyl)hexanoate of formula (III) below, $X_5$ denoting the configuration of the C5 carbon, with $X_5 \neq Xs$ and Y having the same meaning as above,

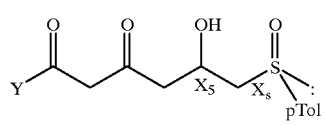

(III)

3) in a third step, the 3-carbonyl function of the alkyl [5($X_5$),S(Xs)]-5-hydroxy-3-oxo-6-(para-tolylsulphinyl)hexanoate is reduced diastereoselectively to obtain the alkyl [3($X_3$),5($X_5$),S(Xs)]-3,5-dihydroxy-6-(para-tolylsulphinyl)hexanoate of formula (IV) below, $X_3$ denoting the configuration of the C3 carbon, choosing a method of reduction that gives $X_5 = X_3$ if an anti configuration is desired or a method of reduction that gives $X_5 \neq X_3$ if a syn configuration is desired for the two alcohol functions, Y having the same meaning as above,

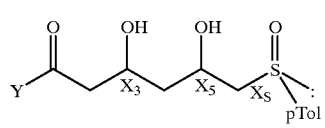

(IV)

4) in a fourth step, the two hydroxyl functions are protected by $C_1$–$C_8$ alkyl radicals or aryl or aralkyl radicals or trialkylsilyl radicals, or by a $C_1$–$C_8$ alkanediyl radical or a benzylidene radical, which radicals will be designated R, to obtain an alkyl [3($X_3$),5($X_5$),S(Xs)]-3,5-dialkyloxy-6-(para-tolylsulphinyl) hexanoate of formula (V) below, Y having the same meaning as above, the said radicals not being displaced under the conditions of steps 5 and 6,

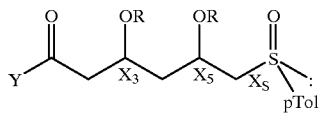

(V)

5) in a fifth step, the sulphoxide function is reduced to thioether by a Pummerer reaction to obtain an alkyl [3($X_3$),5($X_5$)]-6-acetoxy-3,5-dialkyloxy-6-(para-tolylthio)hexanoate of formula (VI) below, R and Y having the same meaning as above,

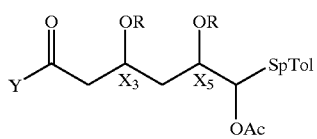

(VI)

6) in a sixth step, the functions at C6 are converted to aldehyde to obtain the alkyl [3($X_3$),5($X_5$)]-6-oxo-3,5-dialkyloxyhexanoate corresponding to the formula (VII), Y and R having the same meaning as above,

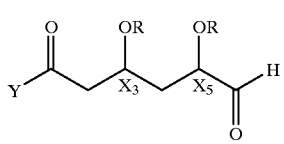

(VII)

7) in a seventh step, the alkyl [3($X_3$),5($X_5$)]-6-oxo-3,5-dialkyloxyhexanoate of formula (VII) is condensed with a Wittig reagent $Ph_3P=CH\Psi$, with $\Psi$ having the definition given above, to give the product of formula (VIII), R and Y having the same meaning as above:

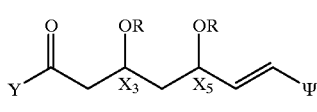

(VIII)

8) in an eighth step, the double bond is reduced to obtain:

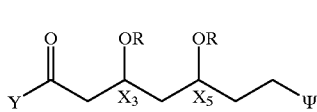

(IX)

9) in a ninth and final step, the protective groups are removed from the hydroxyls, and the ester is hydrolysed to give the product of formula (Ia).

According to a variant of the invention, it is possible, after step 7), to proceed directly to step 9) without reducing the double bond, to obtain the product of formula (Ib).

It is also possible to reverse the order of steps 8 and 9 to gain access to the products of formula (Ia).

Step 1

According to the invention, the tri-anion of the alkyl 3,5-dioxohexanoate of formula (X)

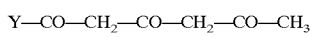

Y—CO—CH$_2$—CO—CH$_2$—CO—CH$_3$ (X)

in which Y has the same definition as above, is reacted with (−)- or (+)-menthyl (X's)-p-toluenesulphinate to obtain the alkyl (Xs)-3,5-dioxo-6-(p-tolylsulphinyl)hexanoate.

Preferably, Y will be chosen from methoxy, ethoxy, tert-butyloxy, 1-imidazolidinyl and benzyloxy radicals and a radical N(OMe)Q, with Q a $C_1$–$C_6$ alkyl radical. On account of its greater ease of preparation and of handling, the advantageous choice is Y=$OCH_3$.

The preparation of methyl 3,5-dioxohexanoate, the starting material, is known; reference may be made, for example, to J. G. Batelan, Synth. Commun. 1976, 6, 81. This method of preparation may be readily applied to other alkyl 3,5-dioxohexanoates.

For the preparation of the products of formula (X) with Y=N(OMe)Q, with Q a $C_1$–$C_6$ alkyl radical, reference may be made to the following documents: S. Nahm and S. M. Weinreb, Tet. Lett. 1981, Vol. 22, 3815–3818; T. A. Oster and T. M. Harris, Tet. Lett. 1983, Vol. 24, 1851–1854.

The tri-anion of the alkyl 3,5-dioxohexanoate is preferably obtained by treatment with sodium hydride and either tert-butyllithium or sec-butyllithium in an anhydrous medium at low temperature. Still more preferably, this reaction is performed in the presence of approximately one equivalent of sodium hydride and two equivalents of tert-butyllithium or in the presence of approximately one equivalent of sodium hydride and two equivalents of sec-butyllithium. Preferably, the reaction is performed in a solvent chosen from ethers, and still more preferably tetrahydrofuran. As a preference, this reaction is performed at a temperature ranging from −10° C. to +10° C. According to a preferred embodiment of the invention, this reaction is carried out at a temperature in the region of 0° C.

Menthyl (X's)-p-toluenesulphinate, with X's=R or S, is known to a person skilled in the art; reference may be made, for example, to G. Solladié, J. Hutt, A. Girardin, Synthesis, 1987, 173. The choice of one or other of the isomers, R or S, of menthyl p-toluenesulphinate depends on the configuration which it is desired to obtain on the C5 carbon after step 2 of reduction of the ketone at C5. According to the invention, the C5 carbon will have the same configuration, $X_5$=X's, as the sulphur of the menthyl (X's)-p-toluenesulphinate. Preferably, this reaction is carried out with an amount of menthyl p-toluenesulphinate substantially equal to 50% in number of moles relative to the number of moles of alkyl 3,5-dioxohexanoate.

It is known that (+)- and (−)-menthol can both yield each of the isomers, R and S, of menthyl p-toluenesulphinate. However, according to G. Solladié, J. Hutt, A. Girardin, Synthesis, 1987, 173, a method of synthesis is known which can be extrapolated to the industrial scale and enables (−)-menthyl (S)-p-(toluenesulphinate to be prepared. This method yields, in an analogous manner, (+)-menthyl (R)-p-toluenesulphinate starting from (+)-menthol. Hence one of these reactants is preferably used. Preferably, it is desired to obtain a product (Ia) or (Ib) having the same configuration as the natural products which are known to be HMG-coenzyme A reductase inhibitors, such as (+)-compactin and (+)-mevinolin. Consequently, menthyl (S)-p-toluenesulphinate is preferably used in the first step and, for the reasons set forth above, (−)-menthyl (S)-p-toluenesulphinate is preferably used.

Step 2

According to the invention, in the second step, the 5-carbonyl function of the alkyl (Xs)-3,5-dioxo-6-(para-tolylsulphinyl)hexanoate is reduced enantioselectively to alcohol to give the alkyl [5($X_5$),S(Xs)]-5-hydroxy-3-oxo-6-(para-tolylsulphinyl)hexanoate, with $X_5 \ne Xs$. Preferably, this reduction is carried out by treating the alkyl (Xs)-3,5-dioxo-6-(p-tolylsulphinyl)hexanoate with a hydride that does not impair the stereochemical induction due to the (Xs)-para-tolylsulphinyl radical and does not reduce the group —COY. In particular, diisobutylaluminium hydride, which satisfies these conditions, may be mentioned. Preferably, this reaction is conducted in an anhydrous medium and the reactants (product of formula II and reducing agent) are introduced at a temperature below −20° C. Still more preferably, this reaction is carried out in tetrahydrofuran and the reactants are introduced at a temperature of −50° C., and still more preferably in the region of −78° C. The medium is then allowed to return to room temperature. The objective of starting the reaction at low temperature is to ensure an exact stereochemistry of C5; however, this condition is not imperative, and some derivatives treated at 0° C. will have the desired stereochemistry.

At the end of this treatment, only the carbonyl at C5 has been reduced, and the reduction has taken place stereoselectively. Thus, the reduction of methyl (R)-3,5-dioxo-6-(p-tolylsulphinyl)hexanoate under the conditions described above gives methyl [5(S),S(R)]-5-hydroxy-3-oxo-6-(para-tolylsulphinyl)hexanoate, and conversely the reduction of methyl (S)-3,5-dioxo-6-(p-tolylsulphinyl)hexanoate gives methyl [5(R),S(S)]-5-hydroxy-3-oxo-6-(para-tolylsulphinyl)hexanoate.

Step 3

According to the invention, in a third step, the 3-carbonyl function of the alkyl [5($X_5$),S(Xs)]-5-hydroxy-3-oxo-6-(para-tolylsulphinyl)hexanoate is reduced diastereoselectively to obtain the alkyl [3($X_3$),5($X_5$),S(Xs)]-3,5-dihydroxy-6-(para-tolylsulphinyl)hexanoate, with the choice of a method of reduction giving $X_5$=$X_3$ if an anti configuration is desired or of a method of reduction giving $X_5 \ne X_3$ if a syn configuration is desired for the two alcohol functions.

Preferably, if it is desired to obtain a syn configuration for the two alcohols, the reduction will be carried out by treating the starting material (formula III) with sodium borohydride in the presence of a chelating agent. Metal derivatives such as, for example, zinc, titanium and boron derivatives may be mentioned among chelating agents. For example, tetraisopropyloxytitanium, zinc bromide or diethylmethoxyborane can be used for this reaction. Preferably, diethylmethoxyborane will be used as chelating agent. Preferably, the reaction is conducted in an anhydrous medium and the reactants (product of formula III, reducing agent and chelating agent) are introduced at a temperature below 0° C. Preferably, this reaction is carried out in the presence of an excess of diethylmethoxyborane and sodium borohydride in tetrahydrofuran, introducing the reactants at a temperature below −20° C. and preferably at −78° C. The objective of starting the reaction at low temperature is to ensure an exact stereochemistry of C3. However, this condition is not imperative, and some derivatives treated at 0° C. will have the desired stereochemistry.

If it is desired to obtain an anti configuration for the two alcohols at C3 and C5, the reduction will preferably be carried out by treating the starting material (product of formula III) with tetramethylammonium triacetoxyborohydride. To carry out this reaction, reference may be made, for example, to G. Solladié, C. Dominguez, J. Org. Chem. 1994, 59, 3898.

Thus, by the choice of the R or S configuration of the menthyl p-toluenesulphinate and the choice of the method of reduction of the third step, the configuration of the C3 and C5 carbons can be fully controlled.

Step 4

According to the invention, in a fourth step, the two hydroxyl functions are protected by $C_1$–$C_8$ alkyl radicals or aryl or aralkyl radicals or trialkylsilyl radicals, or by a $C_1$–$C_8$ alkanediyl radical or a benzylidene radical, which radicals will be designated R. Among the radicals capable of being employed for protecting the two hydroxyl functions, there may be mentioned, for example, methyl, benzyl, tert-butyldimethylsilyl and tert-butyldiphenylsilyl radicals, or isopropylidene and benzylidene radicals, the latter two radicals on their own enabling both hydroxyls to be protected simultaneously. Preferably, for reasons of economy and of ease of handling, an isopropylidene radical is used for this protection. This protection reaction is carried out by means which are well known to a person skilled in the art; the alkyl $[3(X_3),5(X_5),S(Xs)]$-3,5-dihydroxy-6-(para-tolylsulphinyl) hexanoate may, for example, be treated with dimethoxypropane in the presence of catalytic amounts of para-toluenesulphonic acid in acetone.

Step 5

According to the invention, in a fifth step, the sulphoxide function of the product of formula (V) is reduced to thioether by a Pummerer reaction to obtain an alkyl $[3(X_3),5(X_5)]$-6-acetoxy-3,5-dialkyloxy-6-(para-tolylthio)hexanoate. Preferably, this reaction is conducted in acetic anhydride or in trifluoroacetic anhydride, in the presence of a large excess of anhydrous sodium acetate. To carry out this reaction, reference may be made, for example, to Tet. Lett. 23, 5541, 1982.

Step 6

According to the invention, in a sixth step, the functions at C6 of the product of formula (VI) are converted to aldehyde to obtain the alkyl $[3(X_3),5(X_5)]$-6-oxo-3,5-dialkyloxyhexanoate corresponding to the formula (VII). These two reactions may be carried out according to several variants:

6.1) According to a first variant, it is possible:

6.1.a) to reduce the thioether function and hydrolyse the acetate to obtain an alcohol corresponding to the formula (XI):

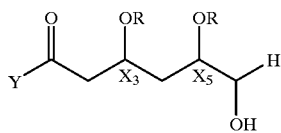

(XI)

and then:

6.1.b) to oxidize the alcohol at C6 to aldehyde. These reactions are well known to a person skilled in the art; for example, the sulphur may be removed by treatment with Raney nickel in a protic solvent such as, for example, methanol, or in ethanol, but it is also possible to carry out this reaction in ethyl acetate; the acetate can then be removed by treating the medium with a base, preferably diisobutylaluminium (DIBAL) carbonate or hydride. Preferably, the sulphur is removed with a large excess of Raney nickel, this amount being adjusted in accordance with the progress of the reaction.

The oxidation of the hydroxyl to aldehyde can be carried out by means which are well known to a person skilled in the art, such as, for example, by the Swern method, for which reference may be made to Mancuso and Swern, Synthesis, 1981, 165–185.

6.2) According to a second variant, the thioether and acetate functions can be converted directly to aldehyde (VII). For example, the product (VI) is treated with a base such as a carbonate in an aqueous medium.

Step 7

According to the invention, in a seventh step, the aldehyde (VII) is condensed with a Wittig reagent $Ph_3P=CH\Psi$. For the preparation of the Wittig reagent and its use, reference may be made to "Advanced Organic Chemistry, Jerry March, 3rd edition, Wiley, 1985, 845–854".

Step 8

The reduction of the double bond which constitutes the eighth step of the process with is the subject of the invention may be carried out by any means known to a person skilled in the art, such as hydrogenation in the presence of a catalyst, for example palladium on charcoal.

Step 9

The ninth step, which consists in deprotecting the protective groups R on the hydroxyls, calls on the knowledge of a person skilled in the art. For example, an acid treatment in an aqueous medium enables isopropylidene and methyl ester groups to be hydrolysed. For deprotection of the products of formula (VIII) or (IX) with Y=N(OMe)Q, with Q a $C_1$–$C_6$ alkyl radical, reference may be made to the following documents: S. Nahm and S. M. Weinreb, Tet. Lett. 1981, Vol. 22, 3815–3818; T. A. Oster and T. M. Harris, Tet. Lett. 1983, Vol. 24, 1851–1854. When the hydroxyl functions are protected by a benzyl or para-nitrobenzyl group, it is possible advantageously to reduce the double bond and deprotect the hydroxyls during the same step. Similarly, when the ester —COY is a benzyl ester, the ester may be hydrolysed at the same time as the double bond is reduced.

The subject of the invention is also:

the alkyl (Xs)-3,5-dioxo-6-(p-tolylsulphinyl)hexanoates of formula (II),

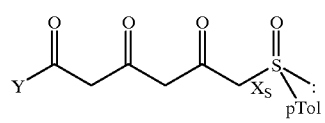

(II)

in which Xs denotes the R or S configuration of the sulphur in the two molecules, Y represents a saturated or unsaturated, linear or branched $C_1$–$C_{18}$ alkyloxy radical, an aryloxy radical or a $C_1$–$C_{18}$ aralkyloxy radical, an imidazolide radical, a saturated or unsaturated, linear or branched $C_1$–$C_{18}$ alkyl sulphide radical, an aryl sulphide or $C_1$–$C_{18}$ aralkyl sulphide radical or a radical

Q denoting a saturated or unsaturated, linear or branched $C_1$–$C_{18}$ alkyl radical, the alkyl $[5(X_5),S(Xs)]$-5-hydroxy-3-oxo-6-(para-tolylsulphinyl)hexanoates of formula (III),

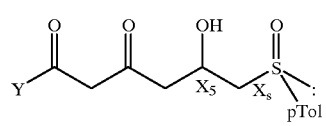

(III)

$X_5$ denoting the configuration of the C5 carbon, with $X_5 \neq Xs$, Xs and Y having the same meaning as above, the alkyl [3($X_3$),5($X_5$),S(Xs)]-3,5-dihydroxy-6-(para-tolylsulphinyl)hexanoates of formula (IV),

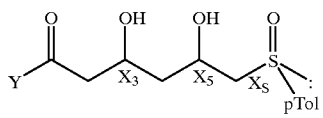

(IV)

$X_3$ denoting the R or S configuration of the C3 carbon, Y, Xs and $X_5$ having the same meaning as above, with $X_3$=$X_5$ or with $X_3 \neq X_5$, the alkyl [3($X_3$),5($X_5$),S(Xs)]-3,5-dialkyloxy-6-(para-tolylsulphinyl)hexanoates of formula

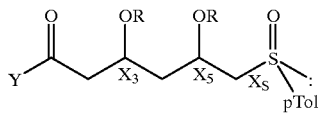

(V)

R representing a $C_1$–$C_8$ alkyl radical or an aryl or $C_1$–$C_8$ aralkyl radical or trialkylsilyl radicals, or a $C_1$–$C_8$ alkanediyl radical or a benzylidene radical, Y, Xs, $X_3$ and $X_5$ having the same meaning as above, the alkyl [3($X_3$),5($X_5$)]-6-acetoxy-3,5-dialkyloxy-6-(para-tolylthio)hexanoates of formula (VI),

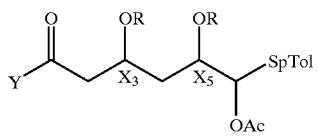

(VI)

R, Y, $X_3$ and $X_5$ having the same meaning as above, the alkyl [3($X_3$),5($X_5$)]-6-oxo-3,5-dialkyloxyhexanoates corresponding to the formula (VII),

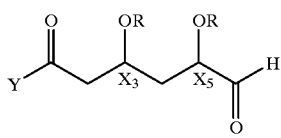

(VII)

Y, R, $X_3$ and $X_5$ having the same meaning as above, the alkyl [3($X_3$),5($X_5$)]-6-acetoxy-3,5-dialkyloxy-6-hydroxyhexanoates of formula (XI),

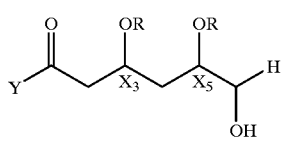

(XI)

in which Y represents a saturated or unsaturated, linear or branched $C_2$–$C_{18}$ alkyloxy radical, an aryloxy radical or a $C_1$–$C_{18}$ aralkyloxy radical, an imidazolide radical, a saturated or unsaturated, linear or branched, $C_1$–$C_{18}$ alkyl sulphide radical, an aryl sulphide or $C_1$–$C_{18}$ aralkyl sulphide radical or a radical

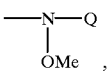

Q denoting a saturated or unsaturated, linear or branched $C_1$–$C_{18}$ alkyl radical, R, $X_3$ and $X_5$ having the same meaning as above.

According to a variant of the invention, the products of formula (Ia) can also be prepared by a process comprising steps 1 to 5 and 6.1.a, characterized in that the triflate or the tosylate of the alcohol (XI) is made, and is then treated with a halide HalΨ, Hal denoting a chlorine, bromine or iodine atom, under conditions which are known to a person skilled in the art for performing the substitution which yields the product (IX):

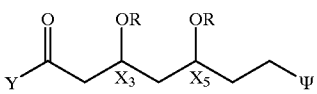

(IX)

This can then be deprotected as described above to give (Ia).

More especially, the subject of the invention is:

methyl (R)-3,5-dioxo-6-(p-tolylsulphinyl)hexanoate (formula II), methyl [5(S),S(R)]-5-hydroxy-3-oxo-6-(para-tolylsulphinyl)hexanoate (formula III), methyl [3(R),5(S),S(R)]-3,5-dihydroxy-6-(para-tolylsulphinyl)hexanoate (formula IV), methyl [3(R),5(S),S(R)]-3,5-isopropylidenedioxy-6-(para-tolylsulphinyl)hexanoate (formula V), methyl [3(R),5(S))-]6-acetoxy-syn-3,5-isopropylidenedioxy-6-(para-tolylthio)hexanoate (formula VI), methyl [3(R),5(S)]-6-oxo-syn-3,5-isopropylidenedioxyhexanoate (formula VII).

The process enabling access to be gained to (4R, 6R)-(+)-4-hydroxy-6-(2-phenylethyl)-tetrahydro-2H-pyran-2-one (2) is given below by way of example in order to illustrate the subject of the invention, without, however, limiting its scope. A scheme corresponding to this process is given in Appendices 1 and 2.

EXAMPLES

NMR spectra are recorded on an instrument of frequency 200 MHz; optical rotation measurements are carried out at 25° C.

Example 1

Synthesis of methyl (R)-(+)-3,5-dioxo-6-(p-tolylsulphinyl)hexanoate (4):

12.1 g (0.0765 mol) of methyl 3,5-dioxohexanoate (6) dissolved in 25 ml of tetrahydrofuran are added dropwise to a suspension, maintained at 0° C., of 2.2 g of NaH (0.95 mol) in 250 ml of tetrahydrofuran. The mixture becomes a thick white suspension, to which 10 g of a 1.5M solution of t-butyllithium in pentane (0.15 mol of t-butyllithium) are added over 15 min at 0° C. using a cannula. During the addition, the solution becomes yellow, then orange, then lastly red. 11.31 g of (−)-menthyl (S)-para-toluenesulphinate (0.038 mol) dissolved in 35 ml of tetrahydrofuran are added dropwise over 20 min. The mixture is stirred for a further approximately 40 min at 0° C. until the sulphinate has disappeared. The medium is then diluted by adding 10 ml of saturated aqueous NH$_4$Cl solution, followed by 250 ml of ethyl acetate, and acidified to pH 1 by adding 170 ml of 1N aqueous hydrochloric acid solution followed by concentrated sulphuric acid. The aqueous phase is extracted three times with 150 ml of ethyl acetate. The organic phases are combined to give a solution which is washed with 100 ml of brine and dried over magnesium sulphate, and the medium is then concentrated under vacuum. The residue is purified by chromatography on silica gel (hexane/CH$_2$Cl$_2$), and then crystallized (CH$_2$Cl$_2$/(CH$_3$CH$_2$)$_2$O) to give 7.73 g of pale yellow crystals.

yield: 68% optical rotation: $[\alpha]_D$=+261 (c=0.98; CHCl$_3$)

melting point: 55–56° C.

$^1$H NMR spectrum (CDCl$_3$): this product is entirely in enol form δ=14.51 (broad s, 1H); δ=7.51 (fragment A of an (AB)$_2$ system, 2H, J$_{AB}$=8 Hz, Δν=37 Hz);. δ=7.32 (fragment B of an (AB)$_2$ system, 2H, J$_{AB}$=8 Hz, Δν=37 Hz); δ=5.65 (s, 1H); δ=3.72 (S, 3H); δ=3.69 (fragment A of an AB system, 1H, J$_{AB}$=14 Hz, Δν=17 Hz); δ=3.58 (fragment B of an AB system, 1H, J$_{AB}$=141 Hz, Δν=17 Hz); δ=3.35 (s, 2H); δ=2.40 (s, 3H).

$^{13}$C NMR spectrum (CDCl$_3$): δ=188.9; δ=179.6; δ=167.4; δ=142.4; δ=139.6; δ=130.2; δ=124.1; δ=102.8; δ=64.9; δ=52.6; δ=45.3; δ=21.6.

Elemental analysis (C$_{14}$H$_{16}$O$_5$S):

|  | C | H |
|---|---|---|
| theoretical: | 56.7 | 5.4 |
| found: | 56.7 | 5.5 |

Example 2

Synthesis of methyl [5(S),S(R)]-(+)-5-hydroxy-3-oxo-6-(para-tolylsulphinyl)hexanoate (7):

40.5 ml of a 1M solution of diisobutylaluminium hydride (DIBAL-H) are added dropwise at −78° C. to a solution of 5.88 g (0.0198 mol) of the product 4 in 350 ml of tetrahydrofuran. After 15 min of stirring, 80 ml of methanol are added. After one hour, the mixture is allowed to return to room temperature, and the solvents are then evaporated off under vacuum to give a fine orange powder which is dissolved in 300 ml of ethyl acetate. To this solution, 20 ml of saturated aqueous disodium L-tartrate dihydrate solution are added. This mixture is stirred for 12 hours at room temperature and then acidified to pH 4 by adding concentrated hydrochloric acid. The aqueous phase is extracted twice with 150 ml of ethyl acetate, then saturated with NaCl and then extracted once with 150 ml of ethyl acetate. The organic phases are combined, this solution is then washed with brine and dried over magnesium sulphate and the medium is concentrated under vacuum. The residue is purified by chromatography on silica gel (hexane/CH$_2$Cl$_2$, 1:1), and then crystallized (CH$_2$Cl$_2$/(CH$_3$CH$_2$)$_2$O) to give 2.61 g of crystals, with an enantiomeric excess d.e.>98%.

yield: 44% optical rotation:

$[\alpha]_D$=+213 (c=1.48; CHCl$_3$);

$[\alpha]_D$=+153 (c=0.90; acetone)

melting point: 120–121° C.

$^1$H NMR spectrum: 9% of enol form identified by a doublet at 4.12 ppm, J=3.4 Hz. δ=7.52 (fragment A of an (AB)$_2$ system, 2H, J$_{AB}$=8 Hz, Δν=33 Hz); δ=7.35 (fragment B of an (AB)$_2$ system, 2H, J$_{AB}$=8 Hz, Δν=33 Hz); δ=4.62 (m, 1H, X part of an ABX system); δ=4.21 (d, 1H, J=2 Hz); δ=3.71 (s, 3H); δ=2.90 (AB part of an ABX system, 2H, J$_{AB}$=13.4 Hz, J$_{AX}$=9.4 Hz, J$_{BX}$=2.4 HZ, Δν=59 Hz); δ=3.47 (s, 2H); δ=2.79 (d, 2H, J=6 Hz); δ=2.42 (s, 3H).

$^{13}$C NMR spectrum (CDCl$_3$): δ32 201.5; δ=167.2; δ=141.8; δ=139.2; δ=130.2; δ=124.0; δ=63.5; δ=60.4; δ=52.5; δ=49.6; δ=49.0; δ=21.4.

Elemental analysis (C$_{14}$H$_{18}$O$_5$S):

|  | C | H |
|---|---|---|
| theoretical: | 56.4 | 6.1 |
| found: | 56.3 | 6.2 |

Example 3

Synthesis of methyl [3(R),5(S),S(R)]-(+)-3,5-dihydroxy-6-(para-tolylsulphinyl)hexanoate (8)

4 ml of a 1M solution of diethylmethoxyborane (4 mmol) in tetrahydrofuran are added rapidly to a solution, cooled to −78° C., of 1.089 g (3.65 mmol) of the product 7 in a mixture of 35 ml of tetrahydrofuran and 7 ml of methanol. This addition causes the appearance of a white precipitate. The mixture is stirred for 20 min, and 178 mg of NaBH$_4$ (4.75 mmol) are then added in a single portion, leading to the production of a homogeneous solution. After 4 h of stirring at −78° C., the solution is allowed to return to room temperature, and 4 ml of acetic acid and 60 ml of saturated aqueous NaHCO$_3$ solution are added, giving a solution of pH 7. The aqueous phase is extracted three times with 150 ml of ethyl acetate. The organic phases are combined, this solution is then washed with brine and dried over magnesium sulphate and the medium is concentrated under vacuum. The residue is a yellow oil which is distilled three times by azeotropic distillation with methanol, and the oil obtained is purified by chromatography on silica gel (ethyl acetate) and is then crystallized at low temperature (4° C.) to obtain 1.09 g of crystals, with an enantiomeric excess d.e.>98%.

yield: 99.4% optical rotation:

$[\alpha]_D$=+220 (c=1.03; CHCl$_3$);

$[\alpha]_D$=+219 (c=0.49; CHCl$_3$)

melting point: 92–94° C.

$^1$H NMR spectrum (CDCl$_3$): δ=7.47 (fragment A of an (AB)$_2$ system, 2H, J$_{AB}$=8 Hz, Δν=39.6 Hz); δ=7.27 (fragment B of an (AB)$_2$ system, 2H, J$_{AB}$=8 Hz, Δν=39.6 Hz); δ=5.05 (broad s, 1H); δ=4.43 (m, 1H); δ=4.27 (m, 2H); δ=3.61 (S, 3H); δ=2.83 (AB part of an ABX system, 2H, J$_{AB}$=13.2 Hz, J$_{AX}$=9.8 Hz, J$_{BX}$=2.5 Hz, Δν=30 Hz); δ=2.43 (d, 2H, J=6 Hz); 67 =2.35 (S, 3H); δ=1.76–1.49 (m, 2H).

$^{13}$C NMR spectrum (CDCl$_3$): δ=172.9; δ=142.2; δ=140.3; δ=130.6; δ=124.5; δ=68.1; δ=66.5; δ=64.2; δ=52.3; δ=42.7; δ=42.2; δ=21.9

Elemental analysis ($C_{14}H_{20}O_5S$)

|  | C | H |
|---|---|---|
| theoretical: | 56.0 | 6.7 |
| found: | 56.2 | 6.7 |

Example 4

Synthesis of methyl [3(R),5(S),S(R)]-(+)-syn-3,5-isopropylidenedioxy-6-(para-tolylsulphinyl)hexanoate (9):

1.17 g of the dihydroxy sulphoxide 8 (3.89 mmol) and 15 mg of para-toluenesulphonic acid (0.13% by weight) are dissolved in 62 ml of acetone and 6.25 ml of 2,2-dimethoxypropane. The mixture is stirred at room temperature for 3 h until the starting material has disappeared. The solvents are evaporated off under vacuum and the crude product is diluted with 100 ml of dichloromethane. To this solution, 10 ml of saturated aqueous $NaHCO_3$ solution are added. The mixture is stirred for 15 min at room temperature and then diluted with 50 ml of water. The aqueous phase is extracted twice with 50 ml of dichloromethane, and all the organic phases are combined, washed with 100 ml of water, dried over magnesium sulphate and concentrated to give 1.3 g of the product 9 in the form of crystals.

yield: 98%
optical rotation: $[\alpha]_D$=+195 (c=1.37; $CHCl_3$)
melting point: 110–111° C.

$^1H$ NMR spectrum ($CDCl_3$):

$\delta$=7.43 (fragment A of an $(AB)_2$ system, 2H, $J_{AB}$=8 Hz, $\Delta v$=42.2 Hz); $\delta$=7.21 (fragment B of an $(AB)_2$ system, 2H, $J_{AB}$=8 Hz, $\Delta v$=42.2 Hz); $\delta$=4.47–4.31 (m, 1H); $\delta$=4.30–4.14 (m, 1H); $\delta$=3.53 (s, 3H); $\delta$=2.43 (m, 2H); $\delta$=2.32 (AB part of an ABX system, 2H, $J_{AB}$=15.6 Hz, $J_{AX}$=7 Hz, $J_{BX}$=6 Hz, $\Delta v$=37.5 Hz); $\delta$=2.26 (s, 3H); $\delta$=1.49 (dt, 1H, $J_{gem}$=12 Hz, $^3J$=2 Hz), $\delta$=1.4 (s, 3H); $\delta$=1.27 (s, 3H); $\delta$=1.27–1.05 (m, 1H).

$^1C$ NMR spectrum ($CDCl_3$): $\delta$=171.2; $\delta$=141.9; $\delta$=141.8; $\delta$=130.3; $\delta$=124.1; $\delta$=99.8; $\delta$=66.0; $\delta$=63.7; $\delta$=65.0; $\delta$=51.9; $\delta$=41.3; $\delta$=36.2; $\delta$=30.2; $\delta$=21.7; $\delta$=20.0.

Elemental analysis ($C_{17}H_{24}O_5S$):

|  | C | H |
|---|---|---|
| theoretical: | 60.0 | 7.1 |
| found: | 60.0 | 7.3 |

Example 5

Synthesis of methyl[3(R),5(S)]-6-acetoxysyn-3,5-isopropylidenedioxy-6-(para-tolylthio)hexanoate (10)

4.4 g of anhydrous sodium acetate (52.8 mmol) are added to 1.8 g (5.28 mmol) of the sulphoxide 9. 130 ml of acetic anhydride are added to the mixture and the whole is brought to reflux for 10 h at 135° C. After cooling, the medium is filtered through Celite and the solvent is evaporated off by azeotropic distillation with toluene. The brown solid which is recovered is diluted in 50 ml of dichloromethane and the solution is filtered through Celite. The crude product is purified by chromatography on silica gel ($CH_2Cl_2$) to give a brown oil, a mixture of the two isomers at position C6 in the proportion 54:46.

$^1H$ NMR spectrum ($CDCl_3$) $\delta$=7.35 (fragment A of an $(AB)_2$ system, 2H, $J_{AB}$=8 Hz, $\Delta v$=56.2 Hz); $\delta$=7.07 (fragment B of an $(AB)_2$ system, 2H, $J_{AB}$=8 Hz, $\Delta v$=56.2 Hz); $\delta$=6 (d, 1H, J=5.4 Hz, preponderant isomer); $\delta$=5.94 (d, 1H, J=5.4 Hz, less abundant isomer); $\delta$=4.30–4.15 (m, 1H); $\delta$=4.10–3.90 (m, 1H); $\delta$=3.64 (s, 3H); $\delta$=2.45 (AB part of an ABX system, 2H, $J_{AB}$=15.8 Hz, $J_{AX}$=7 Hz, $J_{BX}$=6 Hz, $\Delta v$=36.5 Hz); $\delta$=2.28 (s, 3H); $\delta$=2.01 (s, 3H); $\delta$=1.74 (dt, 1H, $J_{gem}$=12.8 Hz, $^3J$=2.4 Hz, preponderant isomer); $\delta$=1.65 (dt, 1H, $J_{gem}$=14.4 Hz, $^3J$=2.4 Hz, less abundant isomer), $\delta$=1.38 (s, 3H, preponderant isomer); $\delta$=1.34 (s, 3H, preponderant isomer); $\delta$=1.36 (s, 3H, less abundant isomer); $\delta$=1.34 (s, 3H, less abundant isomer); $\delta$=1.46–1.22 (m, 1H).

$^{13}C$ NMR spectrum ($CDCl_3$): $\delta$=171.6; $\delta$=170.2; $\delta$=170.0; $\delta$=139.1; $\delta$=139.0; $\delta$=134.7; $\delta$=134.3; $\delta$=130.3; $\delta$=130.2; $\delta$=128.6; $\delta$=128.2; $\delta$=99.9; $\delta$=99.8; $\delta$=83.3; $\delta$=83.1; $\delta$=70.8; $\delta$=70.1; $\delta$=66.0; $\delta$=65.9; $\delta$=51.2; $\delta$=41.5; $\delta$=33.1; $\delta$=32.6; $\delta$=30.3; $\delta$=21.7; $\delta$=21.5; $\delta$=21.4; $\delta$=20.0.

Example 6

Synthesis of methyl [3(R),5(S))]-(+)-6-hydroxy-syn-3,5-isopropylidenedioxyhexanoate (11)

1) First Step

Raney nickel is added portionwise at room temperature to a solution of 1.29 g (3.37 mmol) of 10 in 90 ml of ethanol. The reaction is monitored by slab chromatography on silica (eluent: $AcOEt/CH_2Cl_2$, 1:1). The mixture is filtered through Celite and the solid washed with methanol. The liquid phase is recovered and, after evaporation of the solvents under vacuum, the residue is purified on a silica column (eluent: $AcOEt/CH_2Cl_2$, 1:1). 0.641 g of white crystals of methyl [3(R),5(S)]-(+)-6-acetoxy-3,5-isopropylidenedioxyhexanoate is recovered.

2) Second Step:

706 mg of this product are taken up in 70 ml of methanol. To this solution, 927 mg of $K_2CO_3$ dissolved in 6 ml of water are added dropwise. The initially colourless solution turns yellow and a white precipitate forms. After 3 h of stirring at room temperature, 50 ml of water are added and $NH_4Cl$ is added until a pH of 7 is obtained. The aqueous phase is extracted three times with ethyl acetate, and it is then saturated with NaCl and extracted again three times with ethyl acetate. The organic phases are combined, dried over magnesium sulphate and washed, and the solvents are evaporated off under vacuum to give 459 mg of the product 11 in the form of a colourless liquid.

yield: 78%
optical rotation: $[\alpha]_D$=+9.7 (c=1.85; $CHCl_3$)

$^1H$ NMR spectrum ($CDCl_3$): $\delta$=4.33 (tdd, 1H, J=11.4 Hz, J=6.4 Hz, J=2.6 Hz); $\delta$=4.00 (m, 1H); $\delta$=3.67 (S, 3H); $\delta$=3.53 (AB part of an ABX system, 2H, $J_{AB}$=11.5 Hz, $J_{AX}$=6 Hz, $J_{BX}$=2.5 Hz, $\Delta v$=26 Hz); $\delta$=2.47 (AB part of an ABX system, 2H, $J_{AB}$=15.6 Hz, $J_{AX}$=6.9 Hz, $J_{BX}$=6.1 Hz, $\Delta v$=39 Hz); $\delta$=2.18 (broad s, 1H); $\delta$=1.50 (dt, 1H, $J_{gem}$=13.2 Hz, $^3J$=2.8 Hz), $\delta$=1.46 (s, 3H); $\delta$=1.37 (s, 3H); $\delta$=1.40–1.21 (m, 1H).

$^{13}$C NMR spectrum (CDCl$_3$): δ=171.8; δ=99.5; δ=70.1; δ=66.3; δ=66.0; δ=52.1; δ=41.6; δ=32.4; δ=30.4; δ=20.2.

Elemental analysis (C$_{10}$H$_{18}$O$_5$):

|  | C | H |
|---|---|---|
| theoretical: | 55.0 | 8.3 |
| found: | 54.9 | 8.2 |

Example 7

Synthesis of methyl [3(R),5(R)]-(+)-7-phenyl-3,5-isopropylidenedioxyheptanoate (12):

1) First Step 0.320 ml of DMSO is added dropwise to a solution of 0.2 ml of oxalyl chloride in 5 ml of dichloromethane at −75° C. After 10 min, 156.9 mg (0.718 mmol) of the alcohol 11 diluted in 5 ml of dichloromethane are added slowly to this solution. The heterogeneous mixture is stirred for 1.5 h and the temperature rises to −40° C. The mixture is cooled to −50° C. before 1.2 ml of triethylamine are added, and the mixture is then allowed to return to room temperature with stirring for 1 h. 4 ml of dichloromethane are added in order to solubilize the mixture. The progress of the reaction is monitored by slab chromatography on silica. When the reaction is complete, the medium is diluted with 20 ml of dichloromethane and 20 ml of saturated aqueous NH$_4$Cl solution and then neutralized with 2 ml of 10% aqueous hydrochloric acid solution. The aqueous phase is washed three times with water and with brine and then dried over magnesium sulphate. The solvents are evaporated off under vacuum to give 125 mg of a yellow oil: methyl [3(R),5(S)]-(+)-6-oxo-syn-3,5-isopropylidenedioxyhexanoate.

2) Second Step 0.320 ml of a 1.5M solution of n-butyllithium in hexane is added to a solution containing 204 mg of benzyltriphenylphosphonium bromide in 5 ml of anhydrous tetrahydrofuran. The mixture is stirred for 10 min, and a solution of 90 mg of the aldehyde prepared in the preceding step in 10 ml of anhydrous tetrahydrofuran is then added. The medium is stirred for 4 h at room temperature to give a yellow solution with a white precipitate. 50 ml of dichloromethane are then added, and 60 ml of saturated aqueous NH$_4$Cl solution so that the pH is adjusted to 6. The aqueous phase is extracted twice with 50 ml of dichloromethane and the organic phase is dried over magnesium sulphate, the solvents are then evaporated off and the crude product is purified by chromatography on a silica column (eluent: CH$_2$Cl$_2$). 79.1 mg of methyl [3(R),5(S)]-(+)-7-phenyl-syn-3,5-isopropylidenedioxy-6-heptanoate are then recovered in the form of an 85:15 mixture of Z/E isomers.

3) Third Step

The product prepared in the preceding step (30.4 mg, 0.104 mmol) is reduced in solution in 6 ml of ethyl acetate under hydrogen in the presence of 25 mg of palladium on charcoal (5%) for 24 h. The mixture is then filtered through Celite, washed with dichloromethane and concentrated to give 29.6 mg of methyl [3(R),5(R)]-(+)-7-phenyl-3,5-isopropylidenedioxyheptanoate (12) in the form of a colourless liquid.

yield (three steps): 51% optical rotation: [α]$_D$=+23 (c=1.45; CHCl$_3$)

$^1$H NMR spectrum (CDCl$_3$): δ=7.32–7.13 (m, 5H); δ=4.26 (tdd, 1H, Hx of an ABX system, J=12 Hz, J=6.5 Hz, J=2.6 Hz); δ=3.88–3.75 (m, 1H); δ=3.68 (s, 3H); δ=2.82–2.61 (m, 2H); δ=2.46 (AB part of an ABX system, 2H, J$_{AB}$=15.4 Hz, J$_{AX}$=6.7 Hz, J$_{BX}$=6.3 Hz, Δν=41 Hz); δ=1.93–1.63 (m, 2H); δ=1.56 (dt, 1H, J$_{gem}$=12 Hz, $^3$J=2.6 Hz), δ=1.43 (s, 3H); δ=1.40 (s, 3H); δ=1.33–1.12 (m, 1H).

$^{13}$C NMR spectrum (CDCl$_3$): δ=172.1; δ=142.6; δ=129.2; δ=129.0; δ=126.4; δ=68.2; δ=66.6; δ=52.3; δ=41.9; δ=38.5; δ=37.2; δ=31.7; δ=30.8; δ=20.4.

Elemental analysis (C$_{17}$H$_{24}$O$_4$):

|  | C | H |
|---|---|---|
| theoretical: | 69.8 | 8.3 |
| found: | 69.1 | 8.5 |

Example 8

Synthesis of (4R,6R)-(+)-4-hydroxy-6-(2-phenylethyl)-tetrahydro-2H-pyran-2-one (2)

A solution of 27 mg of the ester 12 in 2 ml of acetic acid and 0.5 ml of water is brought to 92° C. for 2 h. After two hours at room temperature, the solution is diluted with 20 ml of CH$_2$Cl$_2$ and 10 ml of water and then neutralized with saturated aqueous NaHCO$_3$ solution. The aqueous phase is extracted four times with 10 ml of dichloromethane, and the organic phase is washed with brine and dried over magnesium sulphate. The crude product is purified by chromatography on silica. 16 mg of 2 are recovered in the form of crystals, which are recrystallized in a mixture of dichloromethane and hexane.

yield: 81% optical rotation: [α]$_D$=+71 (c=0.94; CHCl$_3$)

melting point: 108° C.

$^1$H NMR spectrum (CDCl$_3$): δ=7.09–7.44 (m, 5H); δ=4.71 (m, 1H); δ=4.37 (m, 1H); δ=2.96=2.64 (m, 4H); δ=2.17–1.69 (m, 4H); δ=2.46 (m, 1H)

$^{13}$C NMR spectrum (CDCl$_3$): δ=171.3; δ=141.7; δ=129.2; δ=129.1; δ=126.8; δ=75.7; δ=63.3; δ=41.7; δ=39.3; δ=38.0; δ=31.8

Elemental analysis (C$_{13}$H$_{16}$O$_3$)

|  | C | H |
|---|---|---|
| theoretical: | 70.9 | 7.4 |
| found: | 70.8 | 7.1 |

Appendix 1
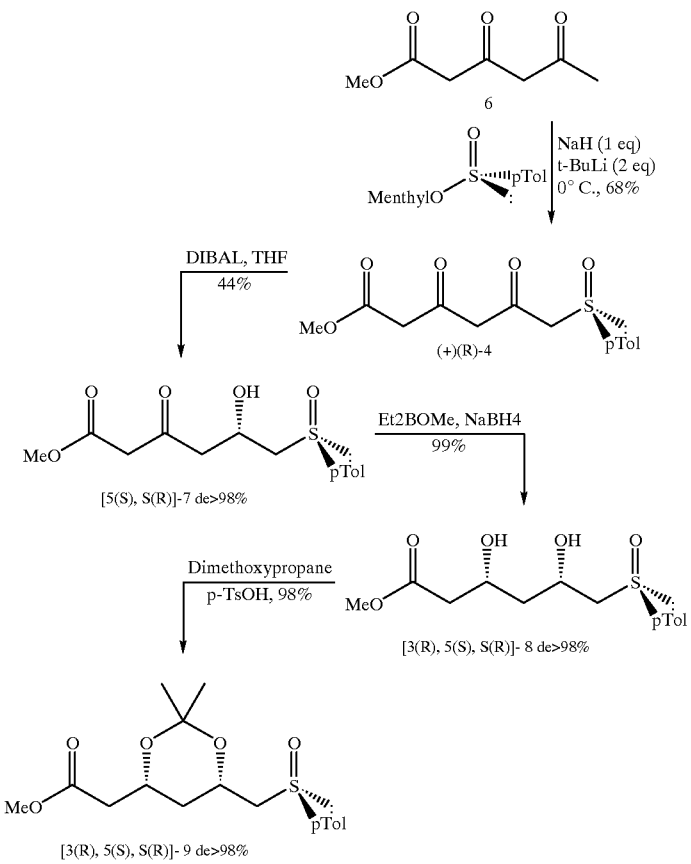
Appendix 2
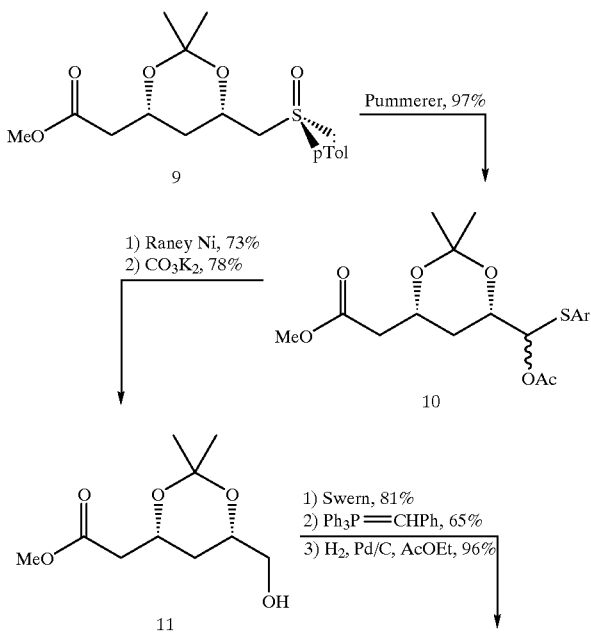

-continued

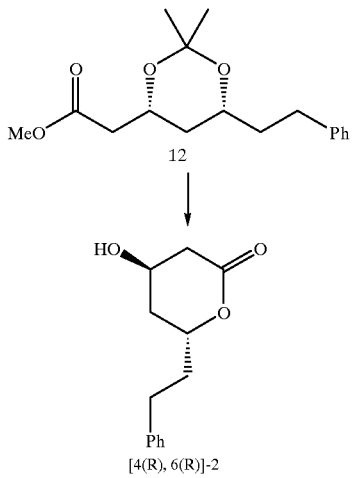

12

↓

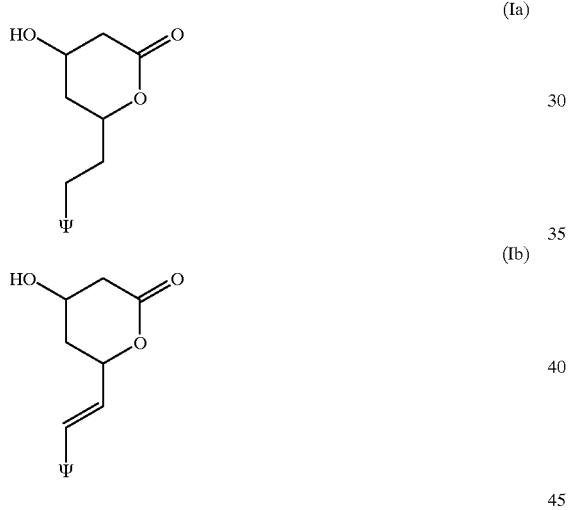

[4(R), 6(R)]-2

What is claimed is:

1. A process for preparing a compound of formula (Ia) or (Ib)

(Ia)

[structure shown]

(Ib)

[structure shown]

wherein ψ is a radical selected from:

saturated or unsaturated, linear, branched or cyclic $C_1$–$C_{40}$ alkyls, optionally containing ether bridges and/or substituted with at least one substituent selected from halogen, hydroxyl, $C_1$–$C_{20}$ alkoxy, $C_1$–$C_{20}$ acyloxy, primary, secondary or tertiary amino, nitro, thiol, carboxyl, amido, $C_1$–$C_{20}$ alkyl carboxylate, aryl carboxylate, $C_1$–$C_{20}$ aralkyl carboxylate, $C_1$–$C_{20}$ alkylamido, arylamido and $C_1$–$C_{20}$ aralkylamido groups, and from aryl radicals and saturated or unsaturated $C_1$–$C_{20}$ nitrogen, oxygen, phosphorus and sulphur heterocycles;

aryls, optionally substituted with at least one substituent selected from halogen, hydroxyl, $C_1$–$C_{20}$ alkoxy, $C_1$–$C_{20}$, acyloxy, amino, $C_1$–$C_{20}$ alkylamino and dialkylamino, nitro, thiol, carboxyl, amido, $C_1$–$C_{20}$ alkyl carboxylate, aryl carboxylate, $C_1$–$C_{20}$ aralkyl carboxylate, $C_1$–$C_{20}$, alkylamido, arylamido, $C_1$–$C_{20}$ aralkylamido and $C_1$–$C_{20}$ aryl groups, and from saturated or unsaturated, linear, branched or cyclic $C_1$–$C_{20}$ alkyl and aralkyl radicals and saturated or unsaturated $C_1$–$C_{20}$ nitrogen, oxygen, phosphorus and sulphur heterocycles;

aralkyls, optionally substituted with at least one substituent selected from halogen, hydroxyl, $C_1$–$C_{20}$ alkoxy, $C_1$–$C_{20}$ acyloxy, amino, $C_1$–$C_{20}$ alkylamino and dialkylamino, nitro, thiol, carboxylic acid, amido, $C_1$–$C_{20}$ alkyl carboxylate, aryl carboxylate, $C_1$–$C_{20}$ aralkyl carboxylate, $C_1$–$C_{20}$ alkylamido, arylamido, $C_1$–$C_{20}$ aralkylamido and $C_1$–$C_{20}$ aryl groups, and from saturated or unsaturated, linear, branched or cyclic $C_1$–$C_{20}$ alkyl and aralkyl radicals; and nitrogen, oxygen or sulphur heterocycles, optionally substituted with at least one substituent selected from halogen, hydroxyl, $C_1$–$C_{20}$ alkoxy, $C_1$–$C_{20}$ acyloxy, primary, secondary or tertiary amino, nitro, thiol, carboxylic acid, amido, $C_1$–$C_{20}$ alkyl carboxylate, aryl carboxylate, $C_1$–$C_{20}$ aralkyl carboxylate, $C_1$–$C_{20}$ alkylamido, arylamido and $C_1$–$C_{20}$ aralkylamido groups, and from aryl and aralkyl radicals and saturated or unsaturated $C_1$–$C_{20}$ nitrogen, oxygen, phosphorus and sulphur heterocycles;

said process comprising at least one of the following steps 1 to 8:

step 1) reacting a tri-anion of an alkyl 3,5-dioxohexanoate compound of formula (X) with (−)- or (+)-menthyl (X's)-p-toluenesulphinate to obtain an alkyl (Xs)-:3,5-dioxo-6-(p-tolylsulphinyl) hexanoate compound of formula (II), wherein formula (X) and formula (II) have the formula:

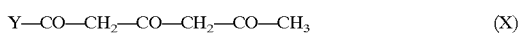

wherein Xs and X's each individually represent the R or S configuration of the sulphur in each of the two molecules (Ia) and (Ib); but wherein Xs does not have the same configuration as X's; and wherein Y is a saturated or unsaturated, linear or branched $C_1$–$C_{18}$ alkyloxy radical; an aryloxy radical or an aralkyloxy radical comprising not more than 18 carbon atoms; an imidazolide radical; a saturated or unsaturated, linear or branched $C_1$–$C_{18}$ alkyl sulphide radical; an aryl sulphide or $C_1$–$C_{20}$ aralkyl sulphide radical, or a radical

wherein Q is a saturated or unsaturated, linear or branched $C_1$–$C_{18}$ alkyl radical;

step 2) reducing the 5-carbonyl function of an alkyl (Xs)-3,5-dioxo-6-(para-tolylsulphinyl)hexanoate compound of formula (II) enantioselectively to alcohol to obtain an alkyl [5($X_5$),S(Xs)]-5-hydroxy-3-oxo-6-(para-tolylsulphinyl)hexanoate compound of formula (III):

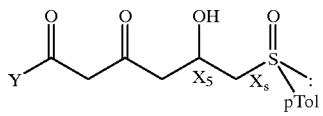

(III)

wherein $X_5$ has the configuration of the C5 carbon; wherein $X_5$ does not have the same configuration as Xs; and wherein Y is a saturated or unsaturated, linear or branched $C_1$–$C_{18}$ alkyloxy radical; an aryloxy radical or an aralkyloxy radical comprising not more than 18 carbon atoms; an imidazolide radical; a saturated or unsaturated, linear or branched $C_1$–$C_{18}$ alkyl sulphide radical; an aryl sulphide or $C_1$–$C_{20}$ aralkyl sulphide radical; or a radical

wherein Q is a saturated or unsaturated, linear or branched $C_1$–$C_{18}$ alkyl radical;

step 3) reducing the 3-carbonyl function of an alkyl [5($X_5$),S(Xs)]-5-hydroxy-3-oxo-6-(para-tolylsulphinyl)hexanoate compound of formula (III) diastereoselectively to obtain an alkyl [3($X_3$),5($X_5$),S(Xs)]-3,5-dihydroxy-6-(para-tolylsulphinyl)hexanoate compound of formula (IV):

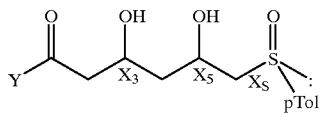

(IV)

wherein $X_3$ has the configuration of the C3 carbon; wherein a method of reduction is used that gives $X_5$ in the same configuration as $X_3$ to obtain an anti configuration or a method of reduction is used that gives $X_5$ not having the same configuration as $X_3$ to obtain a syn configuration for the two alcohol functions; and wherein Y is a saturated or unsaturated, linear or branched $C_1$–$C_{18}$ alkyloxy radical; an aryloxy radical or an aralkyloxy radical comprising not more than 18 carbon atoms; an imidazolide radical; a saturated or unsaturated, linear or branched $C_1$–$C_{18}$ alkyl sulphide radical; an aryl sulphide or $C_1$–$C_{20}$ aralkyl sulphide radical; or a radical

wherein Q is a saturated or unsaturated, linear or branched $C_1$–$C_{18}$, alkyl radical;

step 4) protecting two hydroxyl functions of an alkyl [3($X_3$),5($X_5$),S(Xs)]-3,5dihydroxy-6-(para-tolylsulphinyl)hexanoate compound of formula (IV) with a radical R selected from a $C_1$–$C_8$ alkyl radical, aryl or aralkyl radical, trialkylsilyl radical, a $C_1$–$C_8$ alkanediyl radical and a benzylidene radical, to obtain an alkyl [3($X_3$),5($X_5$),S(Xs)]-3,5-dialkyloxy-6-(para-tolylsulphinyl)hexanoate compound of formula (V):

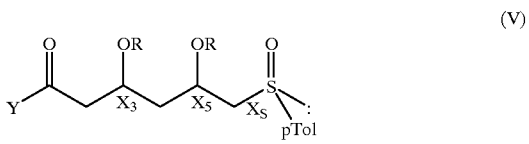

(V)

wherein Y is a saturated or unsaturated, linear or branched $C_1$–$C_{18}$ alkyloxy radical; an aryloxy radical or an aralkyloxy radical comprising not more than 18 carbon atoms; an imidazolide radical; a saturated or unsaturated, linear or branched $C_1$–$C_{18}$ alkyl sulphide radical; an aryl sulphide or $C_1$–$C_{20}$ aralkyl sulphide radical; or a radical

wherein Q is a saturated or unsaturated, linear or branched $C_1$–$C_{18}$ alkyl radical; and the R radical is not displaced under the conditions of steps 5 and 6 below;

step 5) reducing the sulphoxide function of an alkyl [3($X_3$),5($X_5$),S(Xs)]-3,5-dialkyloxy-6-(para-tolylsulphinyl)hexanoate compound of formula (V) to thioether by a Pummerer reaction to obtain an alkyl [3($X_3$),5($X_5$)]-6-acetoxy-3,5-dialkyloxy-6-(para-tolylthio)hexanoate compound of formula (VI):

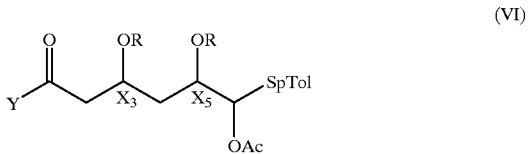

(VI)

wherein R is selected from a $C_1$–$C_8$ alkyl radical, aryl or aralkyl radical, trialkylsilyl radical, a $C_1$–$C_8$ alkanediyl radical and a benzylidene radical; and wherein Y is a saturated or unsaturated, linear or branched $C_1$–$C_{18}$ alkyloxy radical; an aryloxy radical or an aralkyloxy radical comprising not more than 18 carbon atoms; an imidazolide radical; a saturated or unsaturated, linear or branched $C_1$–$C_{18}$ alkyl sulphide radical; an aryl sulphide or $C_1$–$C_{20}$ aralkyl sulphide radical; or a radical

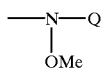

wherein Q is a saturated or unsaturated, linear or branched $C_1$–$C_{18}$ alkyl radical;

step 6) converting the functions at C6 of an alkyl [3($X_3$),5($X_5$)]-6-acetoxy-3,5-dialkyloxy-6-(para-tolylthio)hexanoate compound of formula (VI) to aldehyde to obtain an alkyl [3($X_3$),5($X_5$)]-6-oxo-3,5-dialkyloxyhexanoate compound of formula (VII):

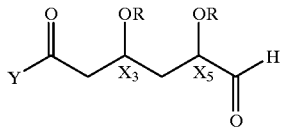

(VII)

wherein Y is a saturated or unsaturated, linear or branched $C_1$–$C_{18}$ alkyloxy radical; an aryloxy radical or an aralkyloxy radical comprising not more than 18 carbon atoms; an imidazolide radical; a saturated or unsaturated, linear or branched $C_1$–$C_{18}$ alkyl sulphide radical; an aryl sulphide or $C_1$–$C_{20}$ aralkyl sulphide radical; or a radical

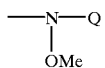

wherein Q is a saturated or unsaturated, linear or branched $C_1$–$C_{18}$ alkyl radical; and wherein R is selected from a $C_1$–$C_8$ alkyl radical, aryl or aralkyl radical, trialkylsilyl radical, a $C_1$–$C_8$ alkanediyl radical and a benzylidene radical;

step 7) condensing the alkyl [3($X_3$),5($X_5$)]-6-oxo-3,5-dialkyloxyhexanote compound of formula (VII) with a Wittig reagent ($Ph_3P=CH\psi$), wherein $\psi$ is a radical selected from:

saturated or unsaturated, linear, branched or cyclic $C_1$–$C_{40}$ alkyls, optionally containing ether bridges and/or substituted with at least one substituent selected from halogen, hydroxyl, $C_1$–$C_{20}$ alkoxy, $C_1$–$C_{20}$ acyloxy, primary, secondary or tertiary amino, nitro, thiol, carboxyl, amido, $C_1$–$C_{20}$ alkyl carboxylate, aryl carboxylate, $C_1$–$C_{20}$ aralkyl carboxylate, $C_1$–$C_{20}$ alkylamido, arylamido and $C_1$–$C_{20}$ aralkylamido groups, and from aryl radicals and saturated or unsaturated $C_1$–$C_{20}$ nitrogen, oxygen, phosphorus and sulphur heterocycles;

aryls, optionally substituted with at least one substituent selected from halogen, hydroxyl, $C_1$–$C_{20}$ alkoxy, $C_1$–$C_{20}$ acyloxy, amino, $C_1$–$C_{20}$ alkylamino and dialkylamino, nitro, thiol, carboxyl, amido, $C_1$–$C_{20}$ alkyl carboxylate, aryl carboxylate, $C_1$–$C_{20}$ aralkyl carboxylate, $C_1$–$C_{20}$ alkylamido, arylamido, $C_1$–$C_{20}$ aralkylamido and $C_1$–$C_{20}$ aryl groups, and from saturated or unsaturated, linear, branched or cyclic $C_1$–$C_{20}$ alkyl and aralkyl radicals and saturated or unsaturated $C_1$–$C_{20}$ nitrogen, oxygen, phosphorus and sulphur heterocycles;

aralkyls, optionally substituted with at least one substituent selected from halogen, hydroxyl, $C_1$–$C_{20}$ alkoxy, $C_1$–$C_{20}$ acyloxy, amino, $C_1$–$C_{20}$ alkylamino and dialkylamino, nitro, thiol, carboxylic acid, amido, $C_1$–$C_{20}$ alkyl carboxylate, aryl carboxylate, $C_1$–$C_{20}$ aralkyl carboxylate, $C_1$–$C_{20}$ alkylamido, arylamido, $C_1$–$C_{20}$ aralkylamido and $C_1$–$C_{20}$ aryl groups, and from saturated or unsaturated, linear, branched or cyclic $C_1$–$C_{20}$ alkyl and aralkyl radicals; and nitrogen, oxygen or sulphur heterocycles, optionally substituted with at least one substituent selected from halogen, hydroxyl, $C_1$–$C_{20}$ alkoxy, $C_1$–$C_{20}$ acyloxy, primary, secondary or tertiary amino, nitro, thiol, carboxylic acid, amido, $C_1$–$C_{20}$ alkyl carboxylate, aryl carboxylate, $C_1$–$C_{20}$ aralkyl carboxylate, $C_1$–$C_{20}$ alkylamido, arylamido and $C_1$–$C_{20}$ aralkylamido groups, and from aryl and aralkyl radicals and saturated or unsaturated $C_1$–$C_{20}$ nitrogen, oxygen, phosphorus and sulphur heterocycles, to yield the compound of formula (VIII):

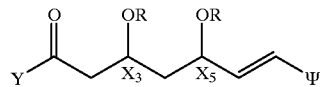

(VIII)

wherein R is selected from a $C_1$–$C_8$ alkyl radical, aryl or aralkyl radical, trialkylsilyl radical, a $C_1$–$C_8$ alkanediyl radical, and a benzylidene radical; and wherein Y is a saturated or unsaturated, linear or branched $C_1$–$C_{18}$ alkyloxy radical; an aryloxy radical or an aralkyloxy radical comprising not more than 18 carbon atoms; an imidazolide radical; a saturated or unsaturated, linear or branched $C_1$–$C_{18}$ alkyl sulphide radical; an aryl sulphide or $C_1$–$C_{20}$ aralkyl sulphide radical; or a radical

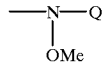

wherein Q is a saturated or unsaturated, linear or branched $C_1$–$C_{18}$ alkyl radical; and step 8) reducing the double bond of a compound of formula (VIII) to obtain a compound of formula (IX):

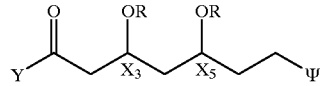

(IX)

and, in a final step 9), removing the protective groups R from the hydroxyls, and hydrolyzing the ester —COY of a compound of formula (VIII) or of a compound of formula (IX) to obtain a compound of formula (Ib) or formula (Ia), respectively.

* * * * *

UNITED STATES PATENT AND TRADEMARK OFFICE
CERTIFICATE OF CORRECTION

PATENT NO. : 6,278,001 B1
DATED : August 21, 2001
INVENTOR(S) : Solladie et al.

It is certified that error appears in the above-identified patent and that said Letters Patent is hereby corrected as shown below:

Column 22, claim 1,
Line 46, delete colon following "(X's)-" and before ":3,5-dioxo-6-(p-tolylsulphinyl)...".

Column 24, claim 1,
Line 8, delete comma following "$C_1$-$C_{18}$".
Line 10, "5dihydroxy" should read -- 5-dihydroxy --.

Signed and Sealed this

Fifth Day of March, 2002

Attest:

JAMES E. ROGAN
Attesting Officer   Director of the United States Patent and Trademark Office